US006293905B1

(12) United States Patent
Saint-Ramon

(10) Patent No.: US 6,293,905 B1
(45) Date of Patent: Sep. 25, 2001

(54) CATHETER FOR ARTIFICIAL INSEMINATION OF BIRDS, IN PARTICULAR TURKEY-HENS, AND METHOD FOR PRODUCING SUCH A CATHETER

(75) Inventor: Jean-Gerard Saint-Ramon, Montmorency (FR)

(73) Assignee: IMV Technologies, L'Aigle (FR)

( * ) Notice: Subject to any disclaimer, the term of this patent is extended or adjusted under 35 U.S.C. 154(b) by 0 days.

(21) Appl. No.: 09/308,157

(22) PCT Filed: Sep. 15, 1998

(86) PCT No.: PCT/FR98/01968

§ 371 Date: May 14, 1999

§ 102(e) Date: May 14, 1999

(87) PCT Pub. No.: WO99/13978

PCT Pub. Date: Mar. 25, 1999

(30) Foreign Application Priority Data

Sep. 16, 1997 (FR) ..................................................... 97 11489

(51) Int. Cl.[7] ..................................................... A61B 5/00

(52) U.S. Cl. ..................................................... 600/35

(58) Field of Search ............................ 600/35, 562, 573; 604/27, 28, 508, 239, 264, 271

(56) References Cited

U.S. PATENT DOCUMENTS 4,628,783 * 12/1986 Brownell et al. ...................... 83/862
5,589,120 * 12/1996 Khan et al. .......................... 264/130

FOREIGN PATENT DOCUMENTS 0 066 488 12/1982 (EP) .
0 084 749 8/1983 (EP) .
1 488 345 10/1967 (FR) .

* cited by examiner

*Primary Examiner*—Max Hindenburg
(74) *Attorney, Agent, or Firm*—Young & Thompson

(57) ABSTRACT

A catheter for artificial insemination of birds includes a plastic tube obtained by extrusion, each of the tube ends is shaped such that the tube's internal diameter at its ends is reduced to a value ranging between two-thirds and three-quarters of the tube's internal diameter, the reduction being obtainable by cold forming at the extruder outlet.

12 Claims, 1 Drawing Sheet

CATHETER FOR ARTIFICIAL INSEMINATION OF BIRDS, IN PARTICULAR TURKEY-HENS, AND METHOD FOR PRODUCING SUCH A CATHETER

BACKGROUND OF THE INVENTION

The present invention concerns storage tubes adapted to contain animal semen and used for artificial insemination, and more particularly catheters for artificial insemination of birds, in particular turkeys.

DESCRIPTION OF THE RELATED ART

Such catheters are well known per se; generally made of a plastics material, their length is in the order of 10 cm, their outside diameter is in the order of 4 mm and their inside diameter is in the order of 3.3 mm throughout the length of the tube, the overall thickness of the wall of the tube being 0.35 mm.

The order of magnitude of the above dimensions responds to various imperatives; such catheters are, of course, suited to the anatomy of turkeys; moreover, firstly, they are designed to be used only once, to prevent contamination; they are therefore designed to contain only one dose of semen; secondly, to simplify handling, given the viscosity of semen, the semen is retained in the tube by capillary action; thirdly, they are suited to filling devices or machines and to emptying devices or guns designed to prevent any contact of the hands with the catheters.

Documents EP-A-0 084 749, EP-A-0 066 488 and FR-A-1 488 345 disclose catheters in which one or each end has an inside diameter that is small compared to the outside diameter of the catheter.

Until now, such catheters have been very useful.

However, because of considerations of economy and therefore of cost-effectiveness, it has become necessary to dilute animal semen increasingly, up to a dilution of two volumes of diluent for one volume of semen, which reduces the viscosity of the semen to a level close to the viscosity of water; the diluted semen can then no longer be retained in the catheter by capillary action.

SUMMARY OF THE INVENTION

One aim of the present invention is to solve this problem simply and at low cost, and to propose a new catheter having all the advantages of the old one, by virtue of keeping general dimensions suiting it to the anatomy of turkeys in particular, containing only one dose of semen and being compatible with existing filling and emptying devices, retaining the semen by capillary action even though the semen is more dilute than in the past.

The invention is based on the observation that, on the one hand, it is easy to reduce the inside diameter of a plastics material tube formed by extrusion by up to two-thirds, or even three-quarters, of the inside diameter of said tube, by simple cold forming at the exit from the extruding machine, and, on the other hand, such reduction is sufficient to solve the problem as stated above encountered with catheters containing dilute semen for artificial insemination of birds, in particular turkeys.

Accordingly, a catheter in accordance with the invention for artificial insemination of birds, in particular turkeys, comprising an extruded plastics material tube, each end of the tube being shaped so that the inside diameter of the tube at its ends is small, is characterized in that the inside diameter of the tube at its ends is reduced to a value in the range from two-thirds to three-quarters the inside diameter of the tube, the reduction possibly being obtained by cold forming at the exit from the extruding machine.

None of the catheters disclosed in the documents cited above has these features; they are suitable only for undiluted semen.

The plastics material of the tube is preferably polyvinyl chloride. Other thermoplastics materials may be suitable, for example polyethylene glycol terephtalate.

Each end preferably has an eyelet obtained by turning in the terminal part of each end.

The outside diameter of the tube is advantageously in the order of 4 mm and its thickness is advantageously in the order of 0.35 mm.

The turned-in part forming the eyelet preferably extends into the tube a distance in the range approximately three times to approximately six times the thickness of the tube; the cylindrical wall of the eyelet facing the inside wall of the tube is pressed against the latter; alternatively, the cylindrical wall of the eyelet facing the inside wall of the tube is at a radial distance from the latter at most equal to seven-tenths the thickness of the tube; the cylindrical wall of the eyelet facing the inside wall of the tube advantageously terminates in a frustoconical part tapering toward the inside of the tube.

In another embodiment, each end has a globally transverse rim.

In a further embodiment, each end has a smaller diameter than the remainder of the tube.

The present invention also consists in a method of producing a catheter for artificial insemination of birds, consisting of a plastics material tube; in accordance with the invention, the method is characterized in that the tube is extruded and each end is cold formed to have the features of the above catheter.

BRIEF DESCRIPTION OF THE DRAWINGS

The features and advantages of the invention will become clear in the course of the following description given by way of example and with reference to the accompanying diagrammatic drawings, in which.

DESCRIPTION OF THE PREFERRED EMBODIMENTS

Figure 1:
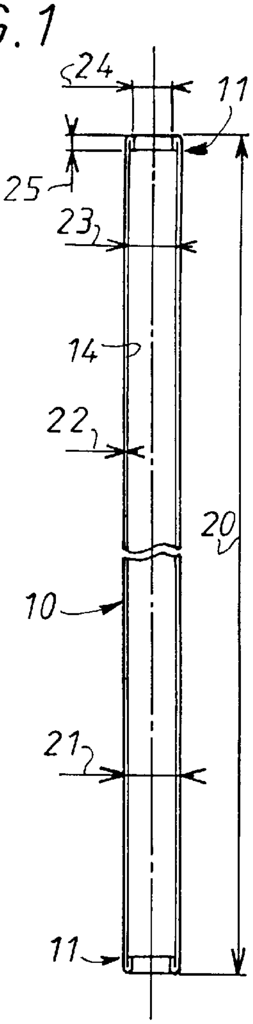
FIG. 1 is a part-sectional view of a catheter in accordance with the invention.

FIG. 1 is a part-sectional view showing a catheter in accordance with the invention for artificial insemination of turkeys in particular. A catheter of this kind globally comprises a plastics material, advantageously polyvinyl chloride, tube 10 having a length 20 in the order of 10 cm, an outside diameter 21 in the order of 4 mm and a thickness 22 in the order of 0.35 mm, and therefore an inside diameter 23 in the order of 3.4 mm.

The diameter 23 usually extends the full length of the tube, which is 103.5 mm, including the ends 11, the edges of which may have been blunted to avoid injuring the turkeys; a catheter of the above kind is very suitable for animal semen whose viscosity is such that it is retained in the tube 10 by capillary action alone; it is therefore not necessary to fit a cap to the end 11 of the tube 10 for transporting and/or manipulating the catheter.

The catheter of the invention is designed to contain dilute animal semen, of reduced viscosity, under the same conditions.

The ends 11 of the tube 10 are therefore shaped in a simple and inexpensive fashion so that the inside diameter 24 of the tube 10 at its ends 11 is reduced by an amount such that the semen is retained by capillary action.

The diameter reduction is advantageously such that the inside diameter 24 of the tube 10 at the ends 11 is reduced to a value in the range from two-thirds to three-quarters the inside diameter 23 of the tube 10.

Accordingly, in the case of a catheter for artificial insemination of turkeys, having the dimensions set out above, the inside diameter 24 of the ends 11 is in the order of 2.2 mm to 2.5 mm.

The diameter is reduced by a simple cold forming operation; the tube 10 is made by extrusion and the cold forming is therefore performed at the exit from the extruding machine.

Figure 2:
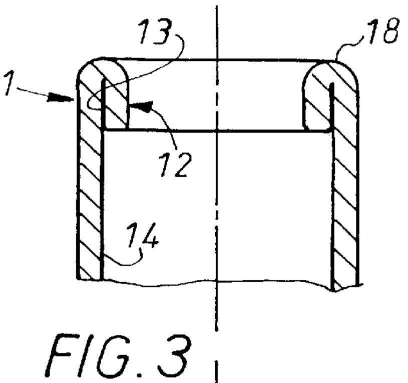
FIG. 2 is a part-sectional view of one end of the catheter from FIG. 1, to a larger scale.

In FIGS. 1 and 2, each end 11 incorporates an eyelet 12 obtained by turning in the terminal part of each end 11; the length 25 of the return forming the eyelet 12 is in the order of three times to six times the thickness of the tube 10, i.e. in the range from 1 mm to 2 mm; note that this method of forming the eyelet 12 forms a rounded end 18, which avoids injury to the animal during artificial insemination; the total length of the catheter is reduced to a value in the order of 101.5 mm; the eyelets 12 at both ends 11 are advantageously formed at the same time, the tube 10 being placed between two crimping wedges; obviously in this case the two eyelets 12 of the same tube 10 may not have exactly equal lengths.

Here the cylindrical wall 13 of the eyelets 12 facing the inside wall 14 of the tube 10 is close to the latter, even pressed against it, extending axially.

Figure 3:
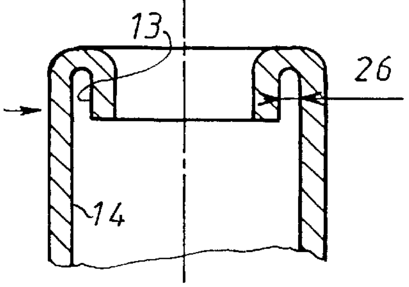
FIG. 3 is a view analogous to FIG. 2 and corresponds to a different embodiment.

In the FIG. 3 embodiment, the cylindrical wall 13 of the eyelet 12 facing the inside wall 14 of the tube 10 is at a radial distance 26 from the latter; this radial distance is small; it is at most equal to 0.25 mm; given the viscosity of semen, even when diluted, semen cannot enter the annular space defined by the facing walls 13 and 14, and there is therefore no loss of semen.

Figure 4:
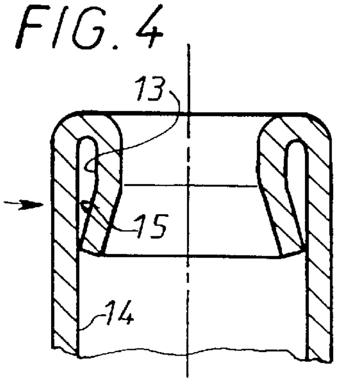
FIG. 4 is a view analogous to FIG. 2 and corresponds to a further embodiment.

In the FIG. 4 embodiment the cylindrical wall 13 of the eyelet 12 facing the inside wall 14 of the tube 10 terminates in a frustoconical part 15 tapering toward the inside of the tube.

Figure 5:
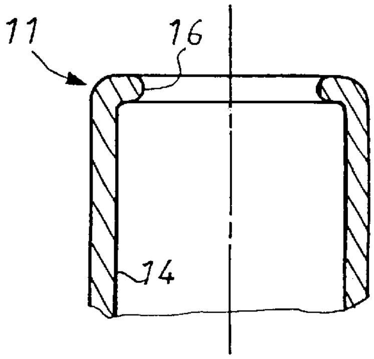
FIG. 5 is a part-sectional view of one end of a variant of the catheter shown in FIGS. 1 to 4.

In the FIG. 5 embodiment, the inside diameter at the ends 11 is reduced by a globally transverse rim 16 with rounded edges.

Figure 6:
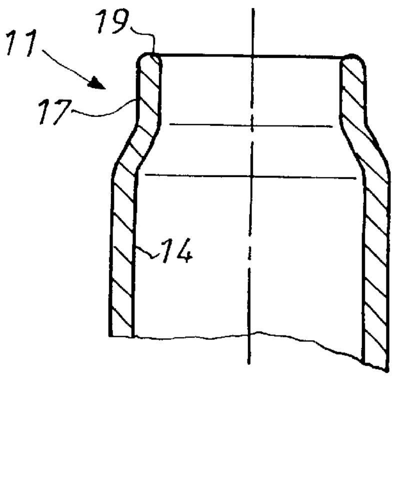
FIG. 6 is analogous to FIG. 5 and shows another embodiment of the catheter.

In the FIG. 6 embodiment, the body of the tube has a reduced diameter 17 at its ends 11; the edge 19 of the ends 11 is advantageously rounded.

What is claimed is:

1. A catheter for artificial insemination of birds comprising:

an extruded plastics material tube, each end (11) of the tube (10) being shaped so that the inside diameter (24) of the tube (10) at its ends (11) is small, wherein the inside diameter (24) of the tube (10) at both of its ends (11) is reduced to a value in the range from two-thirds to three-quarters the inside diameter (23) of the tube (10), the reduction being obtained by cold forming, and the inside diameter of the tube at its ends is sized such that the tube retains by capillarity diluted semen having a viscosity about that of water.

2. A catheter according to claim 1 characterized in that the plastics material of the tube (10) is polyvinyl chloride.

3. A catheter according to claim 1 characterized in that each end (11) incorporates an eyelet (12) obtained by turning in the terminal part of each end (11).

4. A catheter according to claim 1 characterized in that the outside diameter (21) of the tube (10) is in the order of 4 mm and its thickness (22) is in the order of 0.35 mm.

5. A catheter according to claim 3 characterized in that the turned in part of the eyelet (12) extends a distance (25) inside the tube (10) in the range from three times to six times the thickness (22) of the tube (10).

6. A catheter according to claim 3 characterized in that the cylindrical wall (13) of the eyelet (12) facing the inside wall (14) of the tube (10) is pressed against the latter.

7. A catheter according to claim 3 characterized in that the cylindrical wall (13) of the eyelet (12) facing the inside wall (14) of the tube (10) is at a radial distance (26) from the latter at most equal to 7/10 the thickness of the tube (10).

8. A catheter according to claim 7 characterized in that the cylindrical wall (13) of the eyelet (12) facing the inside wall (14) of the tube (10) terminates in a frustoconical part (15) tapering toward the inside of the tube (10).

9. A catheter according to claim 1 characterized in that each end (11) has a globally transverse rim (16).

10. A catheter according to claim 1 characterized in that each end (11) has a smaller diameter (17) than the remainder of the tube (10).

11. A method of producing a catheter for artificial insemination of birds, comprising the steps of:

extruding a plastic tube; and cold forming each of the ends of the plastic tube so that the inside diameter of each end is within a range from two-thirds to three-quarters the inside diameter of the tube and the inside diameter of each end is sized such that the tube retains, by capillarity, diluted semen having a viscosity about that of water.

12. A catheter for artificial insemination of birds comprising:

an extruded plastics material tube, each end (11) of the tube (10) being shaped so that the inside diameter (24) of the tube (10) at its ends (11) is reduced to a value in the range from two-thirds to three-quarters the inside diameter (23) of the tube (10), the reduction being obtained by cold forming, wherein each end (11) incorporates an eyelet (12) obtained by turning in the terminal part of each end (11), and the outside diameter (21) of the tube (10) is in the order of 4 mm and its thickness (22) is in the order of 0.35 mm.

* * * * *